(12) United States Patent
Shah et al.

(10) Patent No.: US 7,970,573 B2
(45) Date of Patent: Jun. 28, 2011

(54) TECHNIQUES FOR DETERMINING ORIENTATION OF A THREE-AXIS ACCELEROMETER

(75) Inventors: Rahul Shah, San Francisco, CA (US); Junaith Ahemed Shahabdeen, San Jose, CA (US); Lama Nachman, Santa Clara, CA (US); Jonathan Huang, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 121 days.

(21) Appl. No.: 12/341,055

(22) Filed: Dec. 22, 2008

(65) Prior Publication Data

US 2010/0161271 A1 Jun. 24, 2010

(51) Int. Cl.
*G01P 15/00* (2006.01)
*G06F 19/00* (2011.01)

(52) U.S. Cl. ...................................... 702/141
(58) Field of Classification Search .............. 702/141, 702/151
See application file for complete search history.

(56) References Cited

U.S. PATENT DOCUMENTS

| | | | | |
|---|---|---|---|---|
| 2006/0161079 | A1* | 7/2006 | Choi et al. | 600/595 |
| 2007/0067139 | A1* | 3/2007 | Kobayashi et al. | 702/150 |
| 2007/0233425 | A1* | 10/2007 | Fujiwara | 702/154 |
| 2008/0288200 | A1* | 11/2008 | Noble | 702/96 |
| 2009/0171615 | A1 | 7/2009 | Shahabdeen et al. | |
| 2010/0030482 | A1* | 2/2010 | Li | 702/19 |

OTHER PUBLICATIONS

Mantyjarvi, et al., "Recognizing Human Motion with Multiple Acceleration Sensors", IEEE International Conference on Systems, Man, and Cybernetics, 2001. vol. 2, pp. 747-752.
Mizell, et al., "Using Gravity to Estimate Accelerometer Orientation", Proceedings of the Seventh IEEE International Symposium on Wearable Computers (ISWC '03). Copyright 2003 IEEE. 2 Pages.
Karantonis, et al., "Implementation of a Real-Time Human Movement Classifier Using a Triaxial Accelerometer for Ambulatory Monitoring", IEEE Transactions on Information Technology in Biomedicine. vol. 10, No. 1, Jan. 2006. pp. 156-167.
Mathie, et al., "Accelerometry: providing an integrated, practical method for long-term, ambulatory monitoring of human movement" Physiological Measurement, vol. 25, Issue 2, pp. R1-R20 (2004).
Tapia, et al., "Activity Recognition in the Home Using Simple and Ubiquitous Sensors", Lecture Notes in Computer Science. Springer Berlin / Heidelberg. vol. 3001/2004. pp. 158-175.

* cited by examiner

*Primary Examiner* — Cindy Hien-Dieu Khuu
(74) *Attorney, Agent, or Firm* — Kacvinsky Daisak PLLC (57) ABSTRACT

A method, apparatus, and article containing computer instructions are described. Embodiments may use accelerometer data regarding forward motion by a wearer of a three-axis on-body accelerometer. Embodiments may further measure an acceleration due to gravity on each axis x, y, z of the accelerometer and use the direction of gravity to associate or align the x axis of the accelerometer with gravity. Embodiments may then use the acceleration not due to gravity to identify the forward motion and associate or align the forward direction with the y axis. The remaining direction may be identified as the sideways direction, which may be associated or aligned with the z axis. Additional activities may then be performed using the now-known orientation of the accelerometer. Other embodiments are described and claimed.

20 Claims, 6 Drawing Sheets

TECHNIQUES FOR DETERMINING ORIENTATION OF A THREE-AXIS ACCELEROMETER

BACKGROUND

Many mobile devices include accelerometers. For example, due to the recent advancement in micro-electrical mechanical systems (MEMS) technologies, MEMS based accelerometers may be integrated into many hand held devices, such as cellular phones and cameras, to improve user interaction. Three-axis accelerometers may also be used to infer a user's physical activity, which may be used for a variety of applications, such as fitness and health monitoring applications, or context-aware applications.

In order to be useful for many applications such as but not limited to activity inference, the initial orientation of the accelerometer must be known. Typically, the orientation may be fixed or determined in advance. Some accelerometers may need to be worn in a precise known location, such as centered on the right side of the waist.

It is with respect to these and other considerations that the following improvements are made.

DETAILED DESCRIPTION

Various embodiments may include one or more techniques for orienting an on-body three-axis accelerometer, regardless of the position of the accelerometer on the body of the wearer.

Recently, Intel Research, of Intel Corporation of Santa Clara, Calif., USA, has developed mobile devices, algorithms and solutions to enable activity inference. For example, the Multi-Sensor Platform (MSP) developed by Intel Research Seattle, is a belt-clip device that may enable activity inference for context aware applications.

Conventionally, for accelerometer based activity recognition systems, the orientation of the device either needs to be fixed or known in advance. For example, some devices only work correctly when mounted on the belt on the right side of the waist, exactly in the center. If the device is not mounted correctly, then it will not be able to distinguish activities correctly, since its reference frame of axes will be different from reality. For example, to distinguish between sitting and standing the system looks at the differences in the orientation of the accelerometer for the two cases (vertical for standing vs. about a 15 degree angle for sitting). To solve this problem, the casing of the device may be designed such that it can only be mounted in one way, and the only variability that can occur is the exact position on the waist; instructions are always given to place it on the right side of the waist, in the center.

To remove the restriction of requiring a fixed method of mounting a three-axis accelerometer to ensure a required frame of reference, embodiments provide techniques to identify the orientation of a three-axis accelerometer automatically, regardless of where the accelerometer is located on the user. Once the orientation is identified, the accelerometer readings can be rotated to the frame of reference desired. This may improve ease of use since the wearer does not need to worry about exact placement of the device.

The techniques described herein may also enable many other methods of activity recognition or other applications that rely on a fixed frame of reference, but are considered as not being practical due to the orientation problem. For example, this can enable the use of three-axis accelerometers on cell-phone class devices that can be carried in the pocket or placed on a person without any regard as to its orientation. This work can be applied to any accelerometer-based device used for activity recognition or other applications where the initial orientation of the accelerometer is important to be known.

Embodiments may rely on a few concepts. A first is that an accelerometer is always subject to an acceleration of 1 g in the downward direction due to gravity. That is used to get a fix on the downward axis. A second concept is that the forward-backward and left-right axes may be identified because these motions are typically orthogonal with each other. A third concept is that humans usually walk or run in the forward direction. Hence, once an accelerometer-based device detects walking or running (recognition that a person is walking or running can be made independently of the frame of reference of the accelerometer-based device), the accelerometer-based device may identify the forward-backward direction. Once two directions are known, the third one can be computed.

Figure 1:
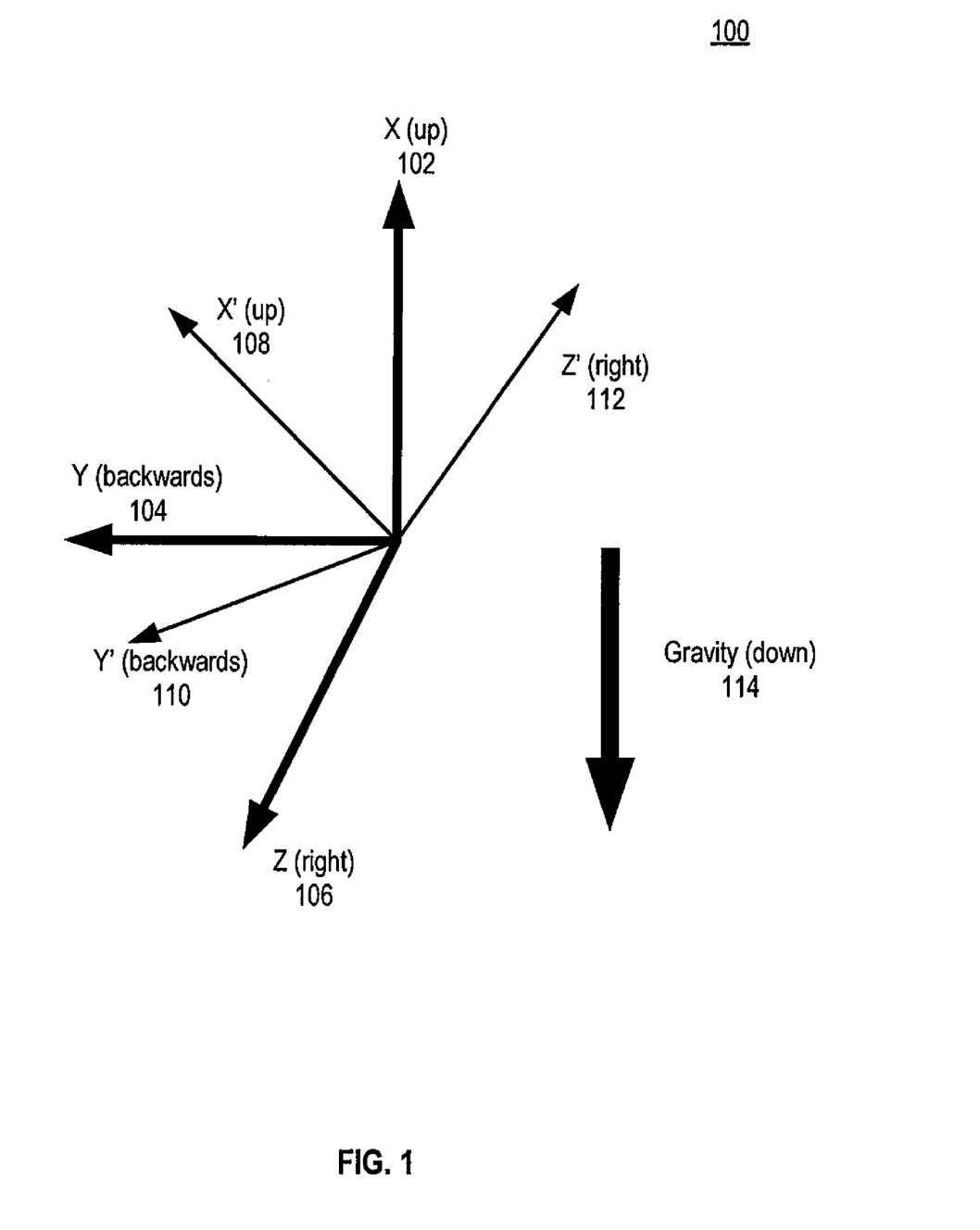
FIG. 1 illustrates a coordinate system for an accelerometer according to embodiments.

FIG. 1 illustrates a coordinate system, as may be defined by an accelerometer-based device. The reference coordinates may define X 102 as up, Y 104 as forward/backward, and Z 106 as right. Gravity 114 is pulling downward by 1 g. Activity classification algorithms or other applications may make the assumption of some fixed coordinate such as this one. The observed coordinate system is one that is measured due to the current orientation of the accelerometer-based device. In FIG. 1, one observed coordinate system may be as shown by X' 108, Y' 110, and Z' 112. Embodiments may rotate the observed coordinate system to the reference coordinate system, such that the activity classification algorithm can have a consistent frame of reference.

Figure 2:
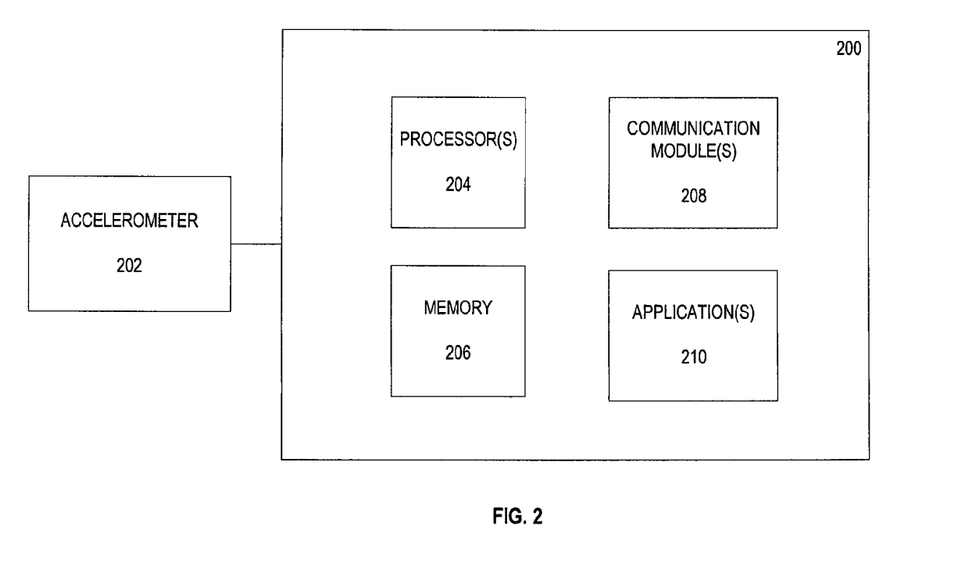
FIG. 2 illustrates an apparatus according to embodiments.

FIG. 2 illustrates a block diagram of an apparatus 200 according to an embodiment. Apparatus 200 may receive acceleration data from accelerometer 202. Apparatus 200 may include one or more processors 204, a memory 206, one or more communications modules 208, and one or more applications 210.

In general, apparatus 200 may comprise various physical and/or logical components for communicating and manipulating information, which may be implemented as hardware components (e.g., computing devices, processors, logic devices), executable computer program instructions (e.g., firmware, software) to be executed by various hardware components, or any combination thereof, as desired for a given set of design parameters or performance constraints. Although FIG. 2 may show a limited number of components by way of example, it can be appreciated that a greater or a fewer number of components may be employed for a given implementation.

In various embodiments, the apparatus 200 may be implemented by a computing platform such as a mobile platform, personal computer (PC) platform, and/or consumer electronics (CE) platform supporting various networking, communications, and/or multimedia capabilities. Such capabilities may be supported by various networks, such as a Wide Area Network (WAN), Local Area Network (LAN), Metropolitan Area Network (MAN), wireless WAN (WWAN), wireless LAN (WLAN), wireless MAN (WMAN), wireless personal area network (WPAN), Worldwide Interoperability for Microwave Access (WiMAX) network, broadband wireless access (BWA) network, the Internet, the World Wide Web, telephone network, radio network, television network, cable network, satellite network such as a direct broadcast satellite (DBS) network, Code Division Multiple Access (CDMA) network, third generation (3G) network such as Wide-band CDMA (WCDMA), fourth generation (4G) network, Time Division Multiple Access (TDMA) network, Extended-TDMA (E-TDMA) cellular radiotelephone network, Global System for Mobile Communications (GSM) network, GSM with General Packet Radio Service (GPRS) systems (GSM/GPRS) network, Synchronous Division Multiple Access (SDMA) network, Time Division Synchronous CDMA (TD-SCDMA) network, Orthogonal Frequency Division Multiplexing (OFDM) network, Orthogonal Frequency Division Multiple Access (OFDMA) network, North American Digital Cellular (NADC) cellular radiotelephone network, Narrowband Advanced Mobile Phone Service (NAMPS) network, Universal Mobile Telephone System (UMTS) network, and/or any other wired or wireless network in accordance with the described embodiments.

In some implementations, the apparatus 200 may comprise a system within and/or coupled to a computing device such as PC, desktop PC, notebook PC, laptop computer, mobile internet device (MID), mobile computing device, smart phone, personal digital assistant (PDA), mobile telephone, combination mobile telephone/PDA, video device, television (TV) device, digital TV (DTV) device, high-definition TV (HDTV) device, media player device, gaming device, or other type of computing device in accordance with the described embodiments. The computing device may include, for example, an electronic display.

A computing device comprising the apparatus 200 may form part of a wired communications system, a wireless communications system, or a combination of both. For example, the computing device may be arranged to communicate information over one or more types of wired communication links. Examples of a wired communication link may include, without limitation, a wire, cable, bus, printed circuit board (PCB), Ethernet connection, peer-to-peer (P2P) connection, backplane, switch fabric, semiconductor material, twisted-pair wire, co-axial cable, fiber optic connection, and so forth. The computing device may be arranged to communicate information over one or more types of wireless communication links. Examples of a wireless communication link may include, without limitation, a radio channel, satellite channel, television channel, broadcast channel infrared channel, radio-frequency (RF) channel, Wireless Fidelity (WiFi) channel, a portion of the RF spectrum, and/or one or more licensed or license-free frequency bands. In wireless implementations, the mobile computing device may comprise one more interfaces and/or components for wireless communication such as one or more transmitters, receivers, transceivers, amplifiers, filters, control logic, wireless network interface cards (WNICs), antennas, and so forth. Although certain embodiments may be illustrated using a particular communications media by way of example, it may be appreciated that the principles and techniques discussed herein may be implemented using various communication media and accompanying technology.

Although certain modules and/or blocks may be described by way of example, it can be appreciated that a greater or lesser number of modules and/or blocks may be used and still fall within the scope of the embodiments. Further, although various embodiments may be described in terms of modules and/or blocks to facilitate description, such modules and/or blocks may be implemented by one or more hardware components (e.g., processors, DSPs, PLDs, ASICs, circuits, registers), software components (e.g., programs, subroutines, logic) and/or combination thereof.

Returning to FIG. 2, processor 204 may execute instructions to perform the techniques described herein. Memory 206 may include, but is not limited to, volatile memory and/or non-volatile memory. Memory 206 may be used to store rotation angles, processor instructions, and other data and instructions to enable the processor to perform the techniques described herein.

Communications modules 208 may include hardware and/or software to enable apparatus 200 to receive data from accelerometer 202, and to communicate with other devices and/or a network. For example, communications modules 208 may receive accelerometer data via a wired connection or via a wireless connection. Communications modules 208 may also provide cellular telephone communications, and/or other data communications for apparatus 200.

Applications 210 may include various software and/or hardware-based applications that provide functionality to apparatus 200. Applications 210 may include an application that orients the accelerometer data. Applications 210 may include, for example, cellular telephone applications, calendar applications, messaging applications, health and fitness applications, geolocation applications, etc. Some applications 210 may use calibrated accelerometer data. For example, a health and fitness application may determine how fast the user is walking or running to calculate calories burned. Examples are not limited to this context.

Figure 3:
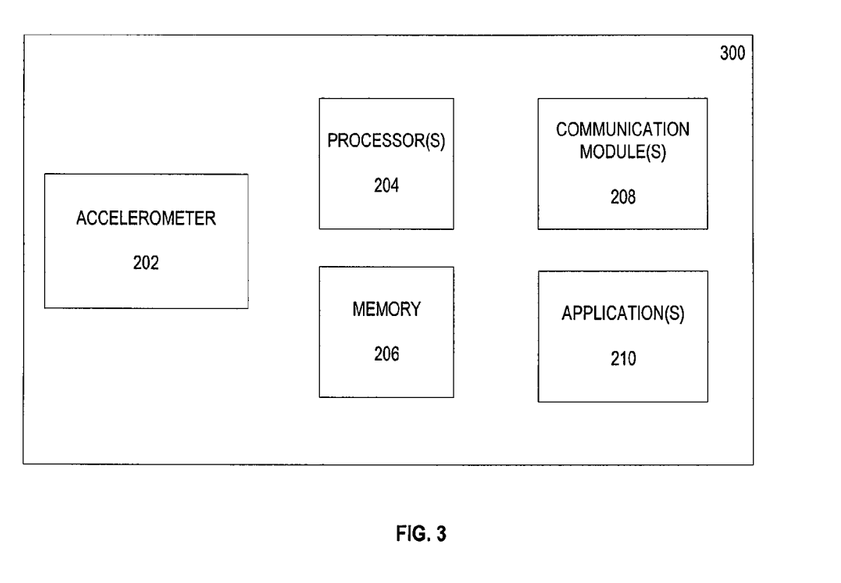
FIG. 3 illustrates an apparatus according to embodiments.

FIG. 3 illustrates an alternate embodiment of an apparatus 300, where accelerometer 202 is included within apparatus 300. Apparatus 300 may be substantially functionally equivalent to the system illustrated in FIG. 2.

Figure 4:
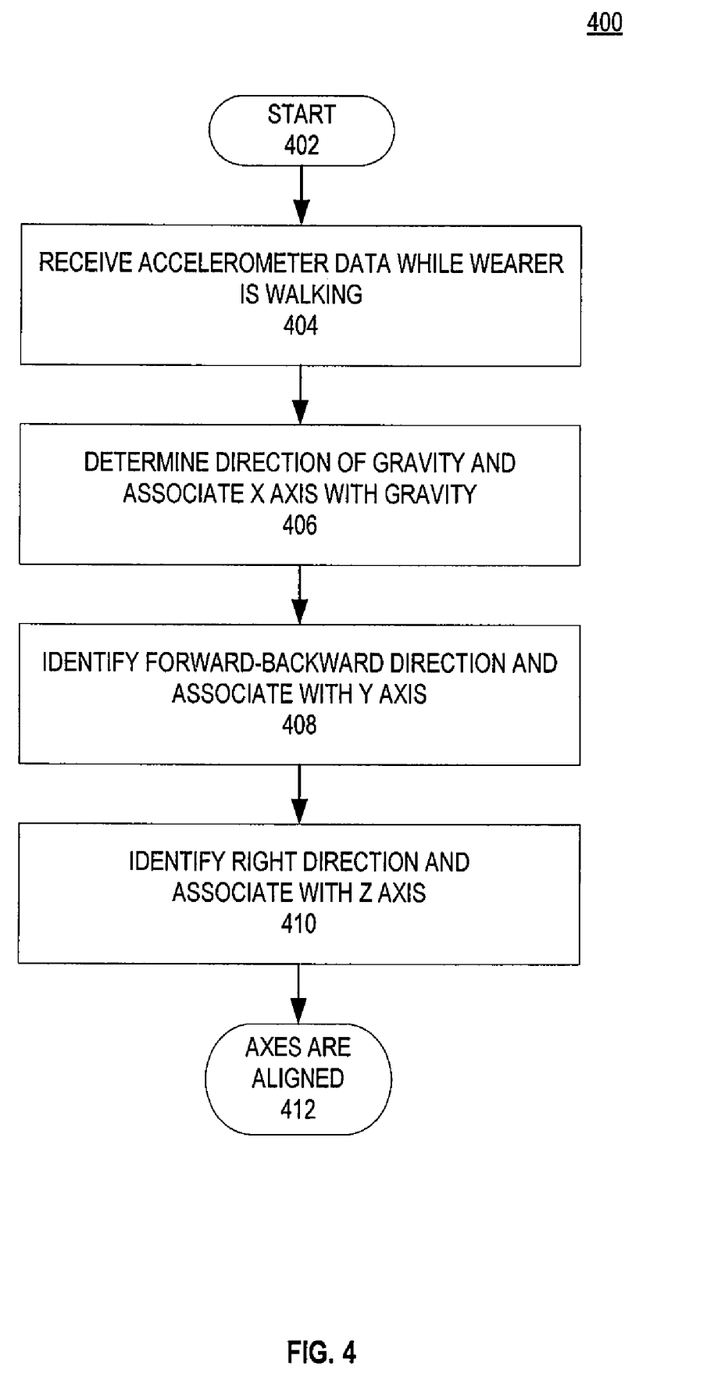
FIG. 4 illustrates a logic flow diagram of a technique for orienting an on-body three-axis accelerometer according to embodiments.

FIG. 4 illustrates a high-level logic flow 400 describing a technique according to one or more embodiments. Beginning at block 402, an apparatus, such as apparatus 200 or 300, may receive accelerometer data in block 404, while the user is walking or running forward. The user may be holding the accelerometer, wearing the accelerometer, or carrying the accelerometer, for example, in a purse or a pocket. As discussed above, the accelerometer may be separate from the apparatus, or a component of the apparatus.

In block 406, the apparatus may determine the direction of acceleration due to gravity, and may associate that direction with the X (up/down) axis. Generally, the mean acceleration measured on a person is about 1 g, which is due to gravity. The force of gravity on a person is also usually the strongest force measured by the accelerometer. This is independent of the activity state (walking, running, standing, etc).

In block 408, the apparatus may determine the forward/backward direction, based on the assumption that most acceleration that is not due to gravity is in the forward direction. The forward/backward direction may be associated with the Y axis.

In block 410, the remaining direction that is perpendicular to the X and Y axes may be identified as the right/left, or sideways, direction. That direction may be associated with the Z axis.

In block 412, the reference axes and observed axes may then be aligned and usable by other applications on the apparatus.

Figure 5:
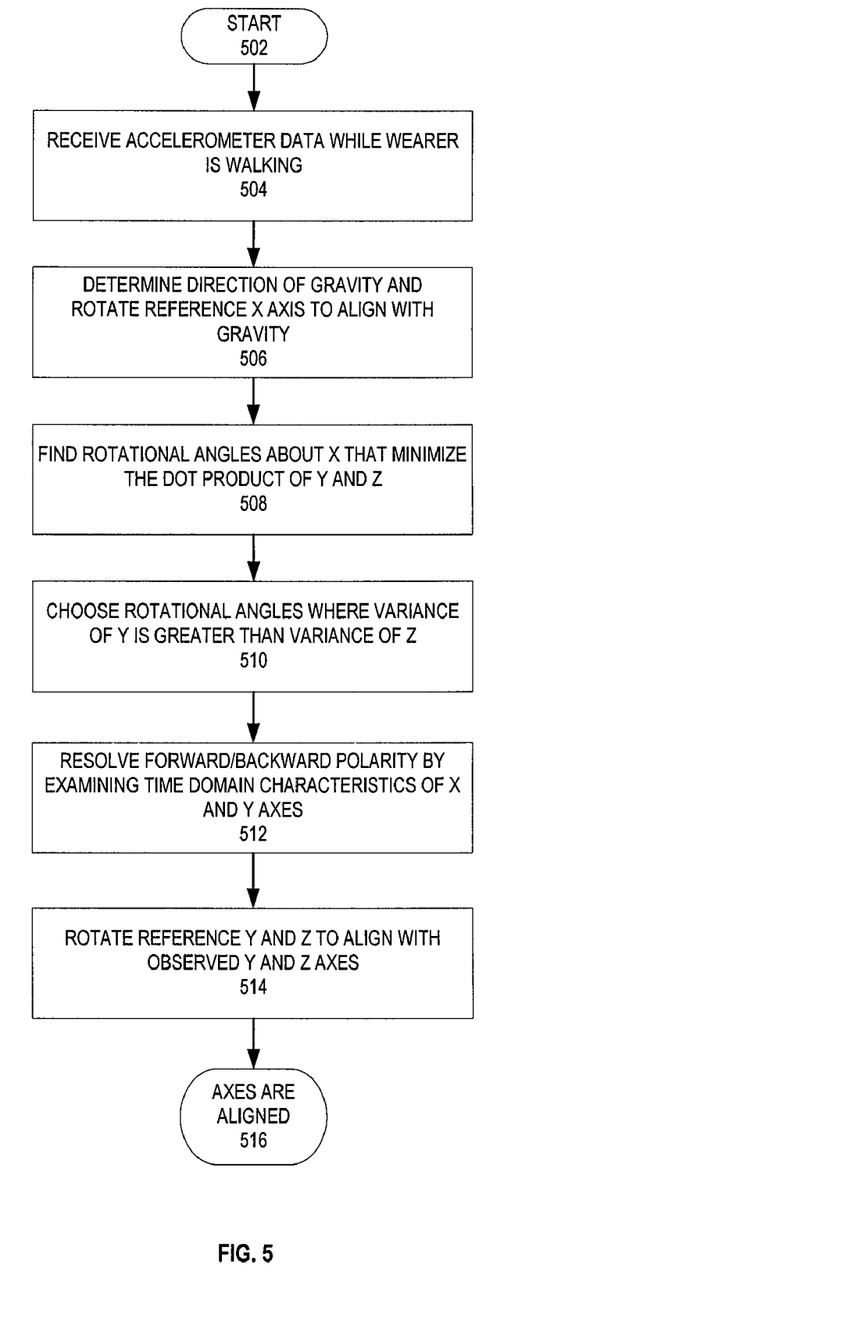
FIG. 5 illustrates a logic flow diagram of a technique for orienting an on-body three-axis accelerometer according to embodiments.

FIG. 5 illustrates a logic flow 500 describing a technique according to one or more embodiments. Beginning in block 502, the apparatus receives accelerometer data while the user is walking in block 504.

In block 506, the apparatus may determine the direction of acceleration due to gravity, and may rotate the reference X axis to align with the direction of gravity. For example, the mean force measured on the three axes prior to rotation may be [X Y Z]=[−0.93249, −0.28129, −0.18089]. The Y and Z values may be nonzero because they are affected by gravity due to the tilt of the coordinate system. The arcsine of the Y and Z components can be used to approximate the angle of rotation on these two axes. As result of this rotation, the corrected force values may be [X Y Z]=[−0.99064, −6.6007e-007, −1.9419e-007]. The rotation about the Y and Z axes are −10.52 and −10.51 degrees, respectively.

Figure 6:
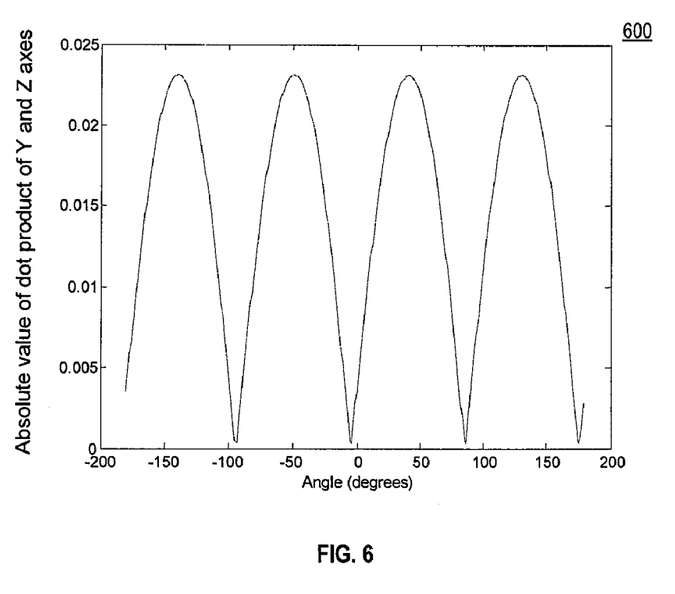
FIG. 6 illustrates a graph of rotational angle plotted against a dot product of the axes being rotated, according to embodiments.

In block 508, the apparatus may identify the rotational angles about X that minimize the dot product of Y and Z. This operation is based on the observation that the forward-backward and left-right motions tend to have lowest correlation when the Y and Z axes are properly aligned. Highly correlated axes share a significant projection of the force vector. When Y and Z are properly aligned, Y will have substantially all of the forward-backward force vector, while Z will have substantially none. To that end, a rotation matrix transformation may be applied about the X axis in the range of angles, e.g. [−180, 180) degrees, in some integer multiple. The absolute value of the dot product of the Y and Z vectors may then be evaluated at each evaluation angle. The angles which minimize this objective function minimize the projection of energy between Y and Z. FIG. 6 shows a graph 600 of an example of the objective function evaluated in the range. There are four minima separated by 90 degrees.

In block 510, the rotational angles that cause the variance of Y to be greater than the variance of Z are chosen. From observations, it is known that the forward-backward motion has far greater variance than the left-right motion when the subject is engaged in forward-moving activities. Therefore, of the four possible minima shown in FIG. 6, the two angle choices that do not fit this pattern may be eliminated by comparing the variance of Y and Z. That is, if var(Y)<var(Z), then eliminate that angle choice. The two remaining angle choices may be snapped onto the reference Y and Z grid, but are opposite in polarity.

In block 512, to resolve the forward-backward polarity, time domain characteristics of the X and Y axes may be examined. Due to the physics of the walking motion, there may be consistent relationships between these two axes that can be captured by the cross-correlation of the two.

Figure 7:
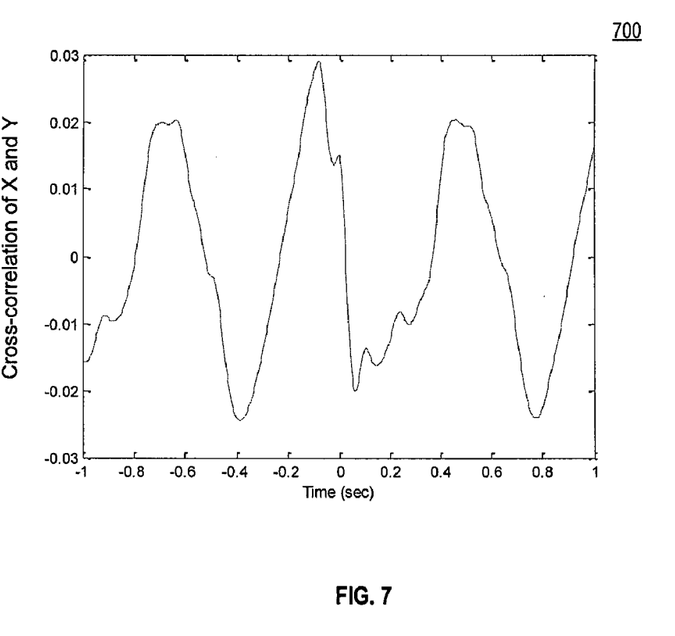
FIG. 7 illustrates a graph of the cross-correlation of two axes over time while forward motion is occurring, according to embodiments.

FIG. 7 shows a graph 700 that plots the cross-correlation of X and Y. In an example, the peak closest to the zero time lag may be shifted to the left, and the slope of the function may be negative around zero. If the polarity were reversed, then the opposite would be true. Generally, if the slope around zero is negative, then the Y axis is forward. If the slope is positive around zero, then the Y axis is backward.

Figure 8:
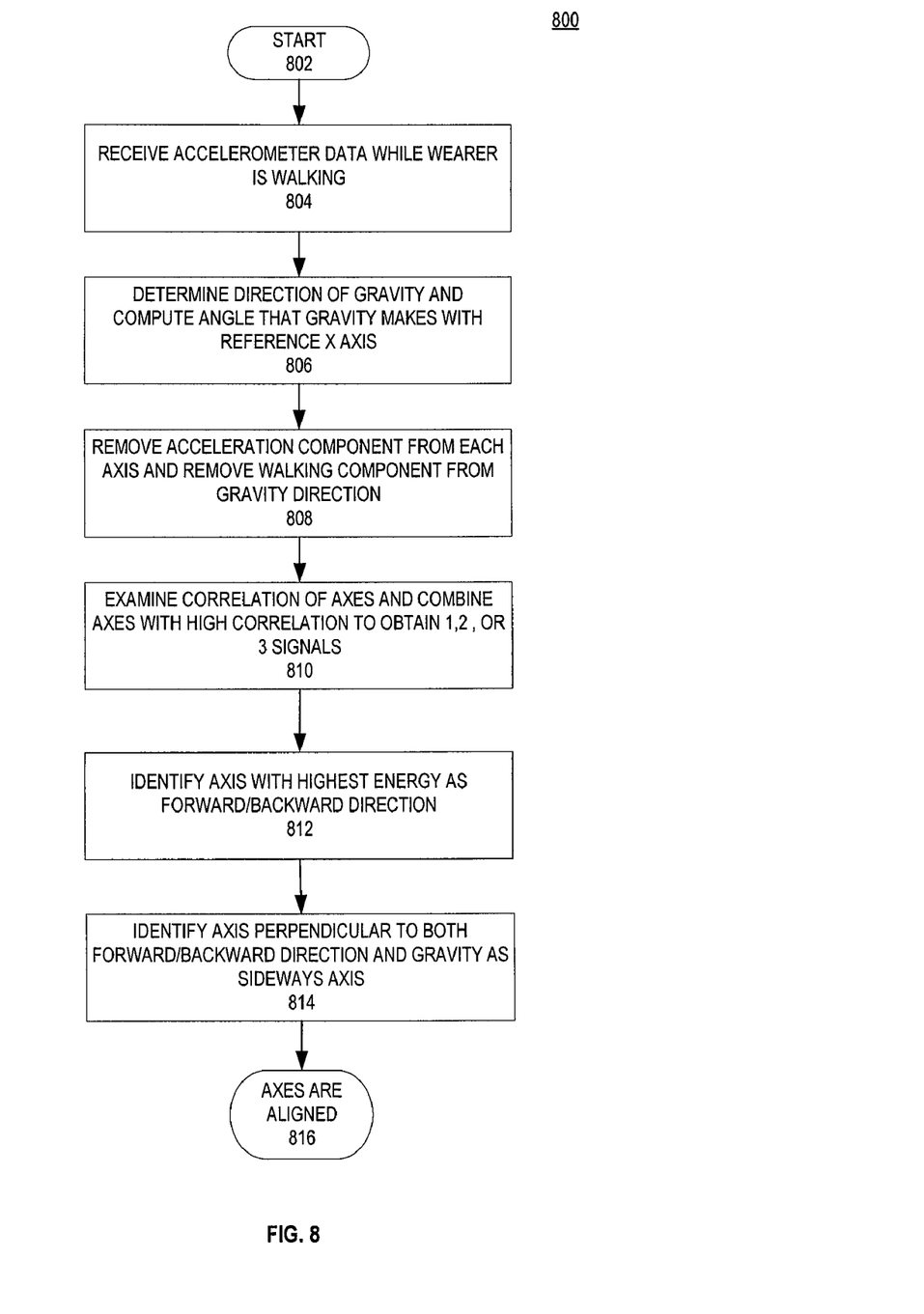
FIG. 8 illustrates a logic flow diagram of a technique for orienting an on-body three-axis accelerometer according to embodiments.

FIG. 8 illustrates a logic flow 800 describing a technique according to one or more embodiments. The technique illustrated in FIG. 8 differs from the one shown in FIG. 5 in that the observed coordinate system is not rotated to the reference coordinate system during the computation. The technique shown in FIG. 8 may determine the angles made by gravity and the forward-backward direction with the observed coordinate system without actually rotating the reference coordinate system. Hence the technique shown in FIG. 8 may be computationally more efficient, while remaining similar in principle to the previous method.

Beginning in block 802, the apparatus receives accelerometer data while the user is walking in block 804.

In block 806, the apparatus may determine the direction of acceleration due to gravity, and may compute the angle that the direction of gravity makes with the reference X axis. The apparatus may determine the mean of the acceleration signal for each of the three axes. This acceleration is primarily the effect of gravity as discussed in the previous method. Thus the mean of the acceleration signal for each of the three axes are the components of gravity. This can be used to compute the angle the gravity makes with the reference axes of the apparatus. If, for example, the net acceleration is a, and the mean of the three axes are $\overline{a_x}$, $\overline{a_y}$ and $\overline{a_z}$. Then the angle gravity makes with the X-axis may be given by $\cos^{-1}(\overline{a_x}/|a|)$. The angle with the Y and Z axes may be computed similarly.

In block 808, the acceleration due to gravity may be removed from the accelerometer data by subtracting the mean value of each axis (determined in block 806) from each sample value. The result may be the acceleration due to walking ($a_{walk}$). The component of the walking signal in the direction of gravity may then be removed, which is a result of the up-down motion during walking. The horizontal acceleration due to walking may be obtained from:

$$a_{walk,horiz} = a_{walk} - \frac{a \cdot a_{walk}}{|a|} * \frac{a}{|a|}$$

The second term in the equation represents the vector projection of $a_{walk}$ in the direction of gravity.

The remaining signal may contain only the acceleration due to walking ($a_{walk,horiz}$) in the horizontal plane. During walking, the energy in the forward-backward direction may be much greater than the energy in the sideways direction. Identifying the accelerometer axis that has the greatest energy may indicate the forward-backward direction. Note that the energy for the x-axis may be determined by $\sqrt{\Sigma a_{x,walk,horiz}^2}$ where the summation is over all the samples. The energy for the Y and Z axes may be computed similarly.

If the accelerometer is oriented such that an accelerometer axis is aligned along the forward-backward direction, then the magnitude of the data for each of the axes may indicate which axis is aligned along the forward-backward direction. For example, if the forward-backward direction is oriented along the Z axis, then the energy in the Z-axis may be much greater. However, if the accelerometer is oriented at an angle to the forward-backward (or sideways) direction, then the energy in the forward-backward (or sideways) direction may be split among the two or three axes that combine for the particular direction.

Therefore, in order to determine the direction of the energy, the apparatus may need to calculate the energy of the signals that is derived by combining the axes appropriately in block 810. To identify which axes to combine, the apparatus may examine the correlation of data for the axes. If the correlation is higher than a threshold, for example, greater than about 0.9, then those axes may be combined. For example, in a scenario where either the forward-backward or sideways direction is split between the X and Z axes, then the correlation of the accelerometer data for the X and Z axes may be very high, while the correlation between the X and Y axes, and the correlation between the Y and Z axes will be much lower. The correlation between two axes may be given by:

$$\text{Correlation between } x \text{ and } z \text{ axis} = \frac{\sum (a_{x,walk,horiz} \cdot a_{z,walk,horiz})}{\sqrt{\sum a_{x,walk,horiz}^2 \cdot \sum a_{z,walk,horiz}^2}}$$

Continuing the above example, the X and Z axes may be combined (call it Signal 1) and the Y axis may be considered separately (call it Signal 2). The X and Z axes may be combined as $\sqrt{\Sigma(a_{x,walk,horiz}^2 + a_{z,walk,horiz}^2)}$.

In block 812, once the axes are combined, the apparatus may identify which axis or signal has the highest energy. The highest energy axis or signal may contain the forward-backward direction. If multiple axes combined for the forward-backward direction, then the ratio of the energy of each of the axes that combined together to the total energy in the forward-backward direction may be the cosine of the angle that the forward-backward direction makes with that axis. So if signal 1 had the higher energy, then the forward-backward direction was split between the X and Z axes. The angle that the forward direction makes with the X axis may be calculated from $\cos^{-1}(a_{x,walk,horiz}/a_{walk,horiz})$. The angle with the Z axis may be computed similarly. This determines the forward-backward direction.

In block 814, the sideways direction may be computed from the known direction of gravity and the forward-backward direction. The sideways direction may be computed from the cross product of the forward-backward and downward direction.

In block 816, all three directions have been computed relative to the three axes of the accelerometer. Data gathered from the accelerometer can be rotated to be along the three directions (forward-backward, sideways, up-down) and any activity recognition algorithm can be applied.

Numerous specific details have been set forth herein to provide a thorough understanding of the embodiments. It will be understood by those skilled in the art, however, that the embodiments may be practiced without these specific details. In other instances, well-known operations, components and circuits have not been described in detail so as not to obscure the embodiments. It can be appreciated that the specific structural and functional details disclosed herein may be representative and do not necessarily limit the scope of the embodiments.

Some of the figures may include a flow diagram. Although such figures may include a particular logic flow, it can be appreciated that the logic flow merely provides an exemplary implementation of the general functionality. Further, the logic flow does not necessarily have to be executed in the order presented unless otherwise indicated.

In various embodiments, the logic flow may comprise, or be implemented as, executable computer program instructions. The executable computer program instructions may be implemented by firmware, software, a module, an application, a program, a subroutine, instructions, an instruction set, computing code, words, values, symbols or combination thereof. The executable computer program instructions may include any suitable type of code, such as source code, compiled code, interpreted code, executable code, static code, dynamic code, and the like. The executable computer program instructions may be implemented according to a predefined computer language, manner or syntax, for instructing a computing device to perform a certain function. The executable computer program instructions may be implemented using any suitable programming language in accordance with the described embodiments. The executable computer program instructions may be provided for download from a server to a computing device such as those described above.

In various embodiments, logic flow may comprise, or be implemented as, executable computer program instructions stored in an article of manufacture and/or computer-readable storage medium implemented by various systems and/or devices in accordance with the described embodiments. The article and/or computer-readable storage medium may store executable computer program instructions that, when executed by a computing device, cause the computing device to perform methods and/or operations in accordance with the described embodiments.

The article and/or computer-readable storage medium may comprise one or more types of computer-readable storage media capable of storing data, including volatile memory or, non-volatile memory, removable or non-removable memory, erasable or non-erasable memory, writeable or re-writeable memory, and so forth. Examples of computer-readable storage media may include, without limitation, random-access memory (RAM), dynamic RAM (DRAM), Double-Data-Rate DRAM (DDRAM), synchronous DRAM (SDRAM), static RAM (SRAM), read-only memory (ROM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory, ovonic memory, ferroelectric memory, silicon-oxide-nitride-oxide-silicon (SONOS) memory, magnetic or optical cards, or any other suitable type of computer-readable media in accordance with the described embodiments.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within computing system registers and/or memories into other data similarly represented as physical quantities within the computing system memories, registers or other such information storage, transmission or display devices.

It is also worthy to note that any reference to "one embodiment" or "an embodiment" means that a particular feature, structure, or characteristic described in connection with the embodiment is included in at least one embodiment. Thus, appearances of the phrases "in one embodiment" or "in an embodiment" in various places throughout the specification are not necessarily all referring to the same embodiment. Furthermore, the particular features, structures or characteristics may be combined in any suitable manner in one or more embodiments.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other.

While certain features of the embodiments have been illustrated as described herein, many modifications, substitutions, changes and equivalents will now occur to those skilled in the art. It is therefore to be understood that the appended claims are intended to cover all such modifications and changes as fall within the true spirit of the embodiments.

The invention claimed is:

1. An apparatus comprising:
   a memory;
   a communications module to receive accelerometer data;
   a processor coupled to the memory and the communications module, the processor operative to:
      determine an acceleration due to gravity from the received accelerometer data on each axis x, y, z of a three-axis on-body accelerometer regarding forward motion by a wearer of the accelerometer;
      associate the x axis with the direction of gravity by rotating the x axis to align with the direction of gravity;
      identify the acceleration due to forward motion by rotating the y and z axes about the x axis until a projection of forward motion between y and z is minimized;
      associate the y axis with the direction of forward motion by rotating the y axis to align with the direction of forward motion;
      identify the sideways direction; and
      associate the z axis with the sideways direction.

2. The apparatus of claim 1, wherein the processor is operative to:
   select the rotation angles that cause the variance of the y axis to be greater than the variance of the z axis; and
   examine time domain characteristics of the cross-correlation of the x and y axes; and
   associate the y axis with the direction of forward motion and z axis with the sideways direction by rotating the y axis to align with the direction of forward motion.

3. The apparatus of claim 1, wherein the processor is further operative to perform activity recognition with the associated axes.

4. The apparatus of claim 1, further comprising the three-axis on-body accelerometer.

5. The apparatus of claim 1, wherein the processor is further operative to associate the x axis with the direction of gravity by calculating the angle ($a_x$) that the x axis makes with the direction of gravity and storing $a_x$ in the memory.

6. The apparatus of claim 5, wherein the processor is further operative to identify the acceleration due to forward motion by:
   removing components of the acceleration due to gravity from each axis;
   removing the vector projection of the motion in the direction of gravity; and
   identifying the axis having the greatest energy as the forward direction.

7. The apparatus of claim 6, wherein the processor is operative to identify the axis having the greatest energy as the forward direction by:
   combining axes having a correlation higher than a threshold;
   identifying the axis or combined axes having the highest energy as the forward direction; and
   examining time domain characteristics of the cross-correlation of the x and y axes; and
   associating the y axis with the direction of forward motion by calculating the angle ($a_y$) that the y axis makes with the direction of forward motion and storing $a_y$ in the memory.

8. The apparatus of claim 7, wherein the processor is operative to:
   identify the sideways direction by calculating the cross-product of the forward direction and the downward direction; and
   associate the z axis with the sideways direction by calculating the angle ($a_z$) the z axis makes with the sideways direction and storing $a_z$ in the memory.

9. A method comprising:
   receiving accelerometer data regarding forward motion by a wearer of a three-axis on-body accelerometer;
   measuring an acceleration due to gravity on each axis x, y, z of the accelerometer;
   associating the direction of gravity with the x axis;
   rotating the x axis to align with the direction of gravity;
   identifying the acceleration due to forward motion;
   rotating the y and z axes about the x axis until a projection of forward motion between y and z is minimized;
   associating the direction of forward motion with the y axis;
   identifying the sideways direction;
   associating the sideways direction with the z axis
   rotating the y axis to align with the direction of forward motion and the z axis with the sideways direction; and
   performing an activity using the associated axes.

10. The method of claim 9, further comprising:
    selecting the rotation angles that cause the variance of the y axis to be greater than the variance of the z axis; and
    examining time domain characteristics of the cross-correlation of the x and y axes.

11. The method of claim 9, further comprising calculating the angle ($a_x$) that the x axis makes with the direction of gravity and storing $a_x$.

12. The method of claim 11, further comprising:
    removing components of the acceleration due to gravity from each axis;
    removing the vector projection of the motion in the direction of gravity;
    identifying the axis having the greatest energy as the forward direction; and
    calculating the angle ($a_y$) that the y axis makes with the direction of forward motion and storing $a_y$.

13. The method of claim 12, further comprising:
    combining axes having a correlation higher than a threshold;
    identifying the axis or combined axes having the highest energy as the forward direction; and
    examining time domain characteristics of the cross-correlation of the x and y axes; and
    calculating the angle ($a_y$) that the y axis makes with the direction of forward motion and storing $a_y$.

14. The method of claim 13, further comprising:
    calculating the cross-product of the forward direction and the downward direction; and
    calculating the angle ($a_z$) the z axis makes with the sideways direction and storing $a_z$.

15. An article comprising a non-transitory computer-readable storage medium containing instructions that when executed by a processor enable a system to:
    receive accelerometer data regarding forward motion by a wearer of a three-axis on-body accelerometer;
    measure an acceleration due to gravity on each axis x, y, z of the accelerometer;
    associate the direction of gravity with the x axis;

rotate the x axis to align with the direction of gravity;
identify the acceleration due to forward motion;
rotate the y and z axes about the x axis until a projection of forward motion between y and z is minimized;
associate the direction of forward motion with the y axis;
identify the sideways direction;
associate the sideways direction with the z axis
rotate the y axis to align with the direction of forward motion and the z axis with the sideways direction; and
perform an activity using the associated axes.

16. The article of claim 15, further comprising instructions that when executed enable the system to:
select the rotation angles that cause the variance of the y axis to be greater than the variance of the z axis;
examine the time domain characteristics of the cross-correlation of the x and y axes.

17. The article of claim 15, further comprising instructions that when executed enable the system to:
calculate the angle ($a_x$) that the x axis makes with the direction of gravity and storing $a_x$.

18. The article of claim 17, further comprising instructions that when executed enable the system to:
remove components of the acceleration due to gravity from each axis;
remove the vector projection of the motion in the direction of gravity;
identify the axis having the greatest energy as the forward direction.

19. The article of claim 18, further comprising instructions that when executed enable the system to:
combine axes having a correlation higher than a threshold;
identify the axis or combined axes having the highest energy as the forward direction; and
examine the time domain characteristics of the cross-correlation of the x and y axes; and
calculate the angle ($a_y$) that the y axis makes with the direction of forward motion and storing $a_y$.

20. The article of claim 18, further comprising instructions that when executed enable the system to:
calculate the cross-product of the forward direction and the downward direction; and
calculate the angle ($a_z$) the z axis makes with the sideways direction and storing $a_z$.

* * * * *